United States Patent [19]

Steger

[11] Patent Number: 4,564,710

[45] Date of Patent: Jan. 14, 1986

[54] PROCESS FOR MAKING MERCAPTO ALCOHOLS

[75] Inventor: Barry N. Steger, Borger, Tex.

[73] Assignee: Phillips Petroleum Company, Bartlesville, Okla.

[21] Appl. No.: 669,558

[22] Filed: Nov. 8, 1984

[51] Int. Cl.$^4$ .......................................... C07C 148/00
[52] U.S. Cl. ...................................................... 568/62
[58] Field of Search .......................................... 568/62

[56] References Cited

U.S. PATENT DOCUMENTS

| 3,394,192 | 7/1968 | Jones | 568/62 |
| 3,710,439 | 1/1976 | Goetze et al. | 568/62 |
| 4,493,938 | 1/1985 | Shimamoto et al. | 568/62 |

Primary Examiner—Donald G. Daus
Assistant Examiner—Mary E. Ceperley
Attorney, Agent, or Firm—Edward L. Bowman

[57] ABSTRACT

A process for the production of mercapto alcohols wherein an epoxide is reacted with excess $H_2S$, the excess $H_2S$ is separated from the mercapto alcohol, and the thus separated $H_2S$ is subjected to reaction conditions sufficient to cause entrained epoxide to be converted to mercapto alcohol before the $H_2S$ is compressed.

10 Claims, No Drawings

PROCESS FOR MAKING MERCAPTO ALCOHOLS

The present invention relates to the production of mercapto alcohols and more particularly to the production of mercapto alcohols in which the —SH and —OH groups are in alpha-beta relationship to each other, by reacting a vicinal epoxide with $H_2S$.

Typically when mercapto alcohols are made in this manner excess $H_2S$ is employed to maximize conversion of the epoxide and to minimize the production of thiodiglycol. In the past the unreacted, excess $H_2S$ was simply flashed to the atmosphere. However, for ecological and economical reasons it is more desirable to recover the $H_2S$ for recycling in the process. The recycling operation generally involves compression and purification of the unreacted $H_2S$.

In practicing the recycling of the unreacted $H_2S$, it was observed that mercapto alcohol built up in the $H_2S$ system knockout pots, compressors, and columns. This in turn led to numerous valve failures in the $H_2S$ compressors. Upon investigation it was surprisingly found that the mercapto alcohol buildup was the result of formation of the mercapto alcohol in the compressors rather than entrainment of the mercapto alcohol in the $H_2S$ stream. The excess $H_2S$ stream coming from the reaction zone was found to contain significant amounts of the epoxide rather than significant amounts of the mercapto alcohol product. The mercapto alcohol was apparently forming as a result of the heat developed during the compression of the $H_2S$.

An object of the present invention is to provide a method for removing the unreacted epoxide from the excess $H_2S$ so that the $H_2S$ can be compressed and purified for reuse without the inconvenience noted in the past.

SUMMARY OF THE INVENTION

In accordance with the present invention a process is provided in which a mercapto alcohol is produced by the reaction of $H_2S$ with a vicinal epoxide under suitable reaction conditions, excess $H_2S$ is separated from the mercapto alcohol and the thus separated excess $H_2S$ prior to being compressed is subjected to reaction conditions sufficient to cause entrained epoxide to be converted to the mercapto alcohol.

DETAILED DESCRIPTION

The reaction of the hydrogen sulfide with the epoxide can be carried out using generally any of the techniques known in the art. Typically examples of such procedures are disclosed in U.S. Pat. Nos. 3,574,768 and 3,462,496, the disclosures of which are incorporated herein by reference. Generally this reaction involves the commingling of a liquid mixture of the epoxide with or without inert diluent with excess $H_2S$.

The epoxides often used in such reactions are alkyl or cycloalkyl epoxides, which can be substituted with halogen groups, alkoxy groups, hydroxyl groups, aromatic groups, such as phenyl, naphthyl, tolyl or hydrocarbon substituted hydrocarbon rings, halo-aromatic groups, and phenoxy and ring-halogenated phenoxy groups.

Specific representative compounds which can be reacted include ethylene oxide, 1,2-propylene oxide, 1,2-butylene oxide, 2,3-butylene oxide, isobutylene oxide, glycidol, butyl glycidyl ether, cyclohexene oxide, styrene oxide, and ring-substituted derivatives thereof, including halogenated and alkylated styrenes, epichlorohydrin, epibromohydrin, epifluorohydrin, epiiodohydrin, diglycidyl ether, and the diglycidyl ether of Bisphenol A.

The present invention is particularly of importance for the reactions using the more volatile epoxides, particularly the alkyl epoxides containing 2 to 6 carbons per molecule, more especially for ethylene oxide and 1,2-propylene oxide.

The temperature and pressures employed in the reaction between the $H_2S$ and the epoxide can vary widely and depend to some extent upon the epoxide employed. Generally, however, the pressure will be in the range of 50 to 1000 psig or more. Generally the temperature is in the range of about 20° C. to about 160° C., more typically in the range of 50° C. to 120° C.

It is generally preferable to employ a catalyst for the reaction between the $H_2S$ and the epoxide. Examples of known catalysts include the activated alumina of U.S. Pat. No. 3,574,768 and those such as alkali metal hydroxides, alkaline earth metal hydroxides, hydrated forms of alkaline earth metal hydroxides, trialkylamines, quaternary amines, and chromium salts of lower saturated aliphatic organic acids having 1 to 4 carbon atoms per molecule.

The amount of the $H_2S$ is as noted greater on a molar basis than the amount of epoxide employed. The mole ratio of $H_2S$ to epoxide can be as high as 10/1 or more.

The unreacted $H_2S$ can be separated from the reaction product in any suitable manner. Typically the separation simply involves venting the $H_2S$ from the first reaction vessel into another vessel or conduit.

Epoxide contained in the separated unreacted excess $H_2S$ can be converted to the mercapto alcohol by heating the mixture to a suitable temperature.

Here again the temperature needed to effect the reaction will vary somewhat depending upon the particular epoxide employed. For $H_2S$ containing entrained ethylene oxide a temperature of at least about 110° F. (43° C.) would generally be desirable. Most typically a temperature of about 140° F. would be preferred.

One preferred technique for effecting the conversion of entrained epoxide to mercapto alcohol involves contacting the $H_2S$ with a heated fluid which is substantially inert, that is to say, a fluid which does not react significantly with the $H_2S$ or epoxide and which does not result in the formation of undesirable byproducts. A particularly preferred fluid for such an embodiment is the mercapto alcohol which results from the reaction of the $H_2S$ and the epoxide. Another example would be suitable thioether, particularly those having no more than about 10 carbon atoms per molecule.

A typical application of the present invention would be in a process wherein ethylene oxide and $H_2S$ are continuously fed into a loop reactor while the mercapto alcohol product is continuously removed. In such a process the pressure in the loop reactor is maintained so that a liquid phase is present and excess $H_2S$ is separated by being flashed to a lower pressure.

Ethylene epoxide entrained in the thus separated $H_2S$ can be converted into additional beta mercapto alcohol by countercurrent contact with the beta mercapto alcohol that had been heated to preferably about 140° F. This can readily be done by passing the $H_2S$ up through a column, preferably containing liquid-gas contacting means or packing, while passing heated mercapto alcohol downward through the column. $H_2S$ substantially free of epoxide can be recovered from the column.

Typically, the H₂S would then be passed through a condenser and a mercapto alcohol accumulator, and then to a compression/purification sytem. The end result is a H₂S stream that can be sent through a compression/purification system without causing the problems heretofore observed. A side benefit is additional mercapto alcohol which can be recovered from the overhead accumulator.

What is claimed is:

1. In a process wherein a mercapto alcohol is produced by the reaction of H₂S with a vicinal epoxide under suitable reaction conditions, excess H₂S is separated from the mercapto alcohol product and compressed for reuse, the improvement comprising subjecting the separated excess H₂S to reaction conditions sufficient to cause entrained epoxide to be converted to the mercapto alcohol before the separated H₂S is subjected to compression.

2. A process according to claim 1 wherein H₂S is reacted with liquid ethylene oxide to produce beta-mercaptoethanol.

3. A process according to claim 2 wherein the separated excess H₂S is contracted with heated beta mercapto ethanol to raise the temperature to a level sufficient to cause entrained ethylene oxide to react with the H₂S.

4. A process according to claim 3 wherein the separated excess H₂S is contacted with a countercurrent flow of the heated beta mercaptoethanol.

5. A process according to claim 4 wherein H₂S and ethylene oxide are reacted in a loop reactor and excess unreacted H₂S is separated by being vented from the loop reactor.

6. A process according to claim 3 wherein H₂S and ethylene oxide are reacted in a loop reactor and excess unreacted H₂S is separated by being vented from the loop reactor.

7. A process according to claim 2 wherein H₂S and ethylene oxide are continuously added to a reaction zone while beta mercapto alcohol is continuously removed.

8. A process according to claim 2 wherein H₂S and ethylene oxide are reacted in a loop reactor and excess unreacted H₂S is separated by being vented from the loop reactor.

9. A process according to claim 1 wherein the separated excess H₂S is contacted with a heated substantially inert fluid to cause the temperature to raise to a level sufficient to cause entrained epoxide to react with the H₂S.

10. A process according to claim 9 wherein the substantially inert fluid comprises the mercapto alcohol which would result from the reaction of H₂S and the alcohol.

* * * * *